United States Patent
Hou (10) Patent No.: US 10,827,994 B2
(45) Date of Patent: Nov. 10, 2020

(54) MEDICAL IMAGING DEVICE AND SUSPENSION GANTRY INCLUDING MULTIPLE SUPPORTING ARMS ROTATABLE RELATIVE TO EACH OTHER

(71) Applicant: BEIJING NEUSOFT MEDICAL EQUIPMENT CO., LTD., Beijing (CN)

(72) Inventor: Xiaofeng Hou, Shenyang (CN)

(73) Assignee: BEIJING NEUSOFT MEDICAL EQUIPMENT CO., LTD., Beijing (CN)

( * ) Notice: Subject to any disclaimer, the term of this patent is extended or adjusted under 35 U.S.C. 154(b) by 292 days.

(21) Appl. No.: 15/476,517

(22) Filed: Mar. 31, 2017

(65) Prior Publication Data

US 2017/0367667 A1 Dec. 28, 2017

(30) Foreign Application Priority Data

Jun. 22, 2016 (CN) .......................... 2016 1 0458104

(51) Int. Cl.
*A61B 6/00* (2006.01)

(52) U.S. Cl.
CPC .............. *A61B 6/4441* (2013.01); *A61B 6/44* (2013.01); *A61B 6/4405* (2013.01); *A61B 6/4411* (2013.01); *A61B 6/4429* (2013.01); *A61B 6/4435* (2013.01); *A61B 6/4447* (2013.01); *A61B 6/4458* (2013.01); *A61B 6/4464* (2013.01); *A61B 6/4482* (2013.01)

(58) Field of Classification Search
CPC ... A61B 6/4435; A61B 6/4441; A61B 6/4447; A61B 6/44; A61B 6/4405; A61B 6/4429; A61B 6/4411; A61B 6/4464; A61B 6/4458

USPC .................................................. 378/196–198
See application file for complete search history.

(56) References Cited

U.S. PATENT DOCUMENTS

| | | | | |
|---|---|---|---|---|
| 5,050,204 A | * | 9/1991 | Siczek | A61B 6/4441 378/196 |
| 6,104,780 A | * | 8/2000 | Hanover | A61B 6/4014 378/101 |
| 6,113,264 A | | 9/2000 | Watanabe | |

(Continued)

FOREIGN PATENT DOCUMENTS

| CN | 202288320 U | 7/2012 |
|---|---|---|
| CN | 103784155 A | 5/2014 |

(Continued)

OTHER PUBLICATIONS

State Intellectual Property Office of the People's Republic of China, Office Action and Search Report issued in counterpart Chinese Application No. 201610458104.6 (dated Jan. 17, 2020) 16 pages (submitted with English-language machine translation).

*Primary Examiner* — Allen C. Ho
(74) *Attorney, Agent, or Firm* — Fish & Richardson P.C.

(57) ABSTRACT

The present disclosure discloses a medical imaging device including a gantry and a first C-arm having an imaging chain. The gantry includes a first supporting arm connecting the first C-arm, a base, a second C-arm connecting the base, and a second supporting arm connecting the second C-arm. The first C-arm may be moveable along the first supporting arm and the second supporting arm may be movable along the second C-arm.

20 Claims, 7 Drawing Sheets

(56) References Cited

U.S. PATENT DOCUMENTS

| | | | | |
|---|---|---|---|---|
| 6,364,526 B2* | 4/2002 | Ivan | A61B 6/4441 | 378/198 |
| 6,382,833 B2* | 5/2002 | Leandersson | A61B 6/4441 | 378/196 |
| 6,412,978 B1* | 7/2002 | Watanabe | A61B 6/105 | 378/196 |
| 6,428,206 B1* | 8/2002 | Watanabe | A61B 6/4233 | 378/197 |
| 6,435,714 B1* | 8/2002 | Bruder | A61B 6/032 | 378/196 |
| 6,461,039 B1* | 10/2002 | Klotz | A61B 6/4441 | 378/196 |
| 6,491,430 B1* | 12/2002 | Seissler | A61B 6/4405 | 348/E5.086 |
| 6,508,586 B2* | 1/2003 | Oota | A61B 6/032 | 378/194 |
| 6,619,840 B2* | 9/2003 | Rasche | A61B 6/032 | 378/196 |
| 6,764,217 B2* | 7/2004 | Yasuda | A61B 6/08 | 378/196 |
| 6,789,941 B1* | 9/2004 | Grady | A61B 6/4233 | 378/196 |
| 6,811,313 B2* | 11/2004 | Graumann | A61B 6/4233 | 378/167 |
| 7,052,421 B2* | 5/2006 | Simmons | A61B 6/4405 | 378/197 |
| 7,086,779 B2* | 8/2006 | Fadler | A61B 6/0457 | 378/196 |
| 7,168,855 B2* | 1/2007 | Engström | A61B 6/4441 | 378/196 |
| 7,261,464 B2* | 8/2007 | Noda | A61B 6/4441 | 378/195 |
| 7,300,204 B2* | 11/2007 | Gotoh | A61B 6/4441 | 378/197 |
| 7,300,205 B2* | 11/2007 | Grady | A61B 6/4405 | 378/197 |
| 7,534,036 B2* | 5/2009 | Delmas | A61B 6/4441 | 378/196 |
| 7,543,986 B2* | 6/2009 | Saffer | A61B 6/4441 | 378/196 |
| 7,578,618 B2* | 8/2009 | Timmermans | A61B 6/4441 | 378/197 |
| 7,591,587 B2* | 9/2009 | Gotoh | A61B 6/4441 | 378/189 |
| 7,594,751 B2* | 9/2009 | Grebner | A61B 6/4014 | 378/196 |
| 7,597,473 B2* | 10/2009 | Graumann | A61B 6/4441 | 378/196 |
| 7,607,832 B2* | 10/2009 | Jensen | A61B 6/4405 | 378/197 |
| 7,634,308 B2* | 12/2009 | Ogawa | A61B 6/481 | 378/196 |
| 7,658,540 B2* | 2/2010 | Jensen | A61B 6/4405 | 378/197 |
| 8,297,839 B2* | 10/2012 | Tsujii | A61B 6/4405 | 378/197 |
| 8,351,574 B2* | 1/2013 | Takemoto | A61B 5/02007 | 378/4 |
| 8,408,788 B2* | 4/2013 | Ozawa | A61B 6/102 | 378/197 |
| 8,591,107 B2* | 11/2013 | Peters | A61B 6/4441 | 378/193 |
| 8,781,068 B2* | 7/2014 | Noda | A61B 6/4233 | 378/19 |
| 8,794,832 B2* | 8/2014 | Noda | A61B 6/4441 | 378/193 |
| 8,849,370 B2* | 9/2014 | Bouvier | A61B 6/102 | 600/407 |
| 8,944,680 B2* | 2/2015 | Graumann | A61B 6/4452 | 250/491.1 |
| 8,961,009 B2* | 2/2015 | Altvater | A61B 6/4441 | 378/197 |
| 8,992,082 B2* | 3/2015 | Zhang | A61B 6/4429 | 378/197 |
| 9,033,575 B2* | 5/2015 | Martinez Ferreira | A61B 6/587 | 378/197 |
| 9,036,769 B2* | 5/2015 | Noguchi | A61B 6/4464 | 378/8 |
| 9,125,611 B2* | 9/2015 | Eaves | A61B 6/4405 | |
| 9,173,628 B2* | 11/2015 | Bouvier | A61B 6/4405 | |
| 9,220,471 B2* | 12/2015 | Noda | A61B 6/4233 | |
| 9,480,437 B2* | 11/2016 | Watanabe | A61B 6/022 | |
| 9,492,131 B2* | 11/2016 | Meek | A61B 6/4476 | |
| 9,532,757 B2* | 1/2017 | Claus | A61B 6/032 | |
| 9,554,761 B2* | 1/2017 | Baumann | A61B 6/4441 | |
| 9,730,653 B2* | 8/2017 | Niizeki | A61B 6/4441 | |
| 9,737,275 B2* | 8/2017 | Noda | A61B 6/4441 | |
| 9,801,598 B2* | 10/2017 | Zaiki | A61B 6/4441 | |
| 9,855,015 B2* | 1/2018 | Risher-Kelly | A61B 6/032 | |
| 9,855,016 B2* | 1/2018 | Lee | A61B 6/4441 | |
| 9,888,892 B2* | 2/2018 | Abe | A61B 6/466 | |
| 9,907,522 B2* | 3/2018 | Lee | A61B 6/4429 | |
| 9,913,623 B2* | 3/2018 | Ohishi | A61B 6/4441 | |
| 9,931,091 B2* | 4/2018 | Watanabe | A61B 6/463 | |
| 9,936,928 B2* | 4/2018 | Wakai | A61B 6/487 | |
| 9,962,139 B2* | 5/2018 | Kojima | A61B 6/0457 | |
| 9,986,959 B2* | 6/2018 | Atzinger | A61B 6/4441 | |
| 9,997,269 B2* | 6/2018 | Roh | A61B 6/405 | |
| 10,028,713 B2* | 7/2018 | Risher-Kelly | A61B 6/035 | |
| 10,080,532 B2* | 9/2018 | Ohishi | A61B 6/487 | |
| 10,080,536 B2* | 9/2018 | Margot | A61B 6/4405 | |
| 10,172,574 B2* | 1/2019 | Schäfer | A61B 6/0492 | |
| 10,213,171 B2* | 2/2019 | Masuo | A61B 6/08 | |
| 10,271,804 B2* | 4/2019 | Ohga | A61B 6/469 | |
| 10,271,808 B2* | 4/2019 | Auvray | A61B 6/032 | |
| 10,278,654 B2* | 5/2019 | Sadakane | A61B 6/4417 | |
| 10,285,660 B2* | 5/2019 | Zaiki | A61B 6/4429 | |
| 10,292,673 B2* | 5/2019 | Niizeki | A61B 6/4405 | |
| 10,307,121 B2* | 6/2019 | Brudniok | A61B 6/4441 | |
| 10,314,554 B2* | 6/2019 | Hoornaert | A61B 6/06 | |
| 10,368,816 B2* | 8/2019 | Bouvier | A61B 6/10 | |
| 10,405,821 B2* | 9/2019 | Hansis | A61B 5/4566 | |
| 10,441,239 B2* | 10/2019 | Abe | A61B 6/4441 | |
| 10,448,910 B2* | 10/2019 | Johnson | A61B 6/4405 | |
| 10,499,868 B2* | 12/2019 | Akiyama | A61B 6/12 | |
| 10,506,997 B2* | 12/2019 | Fuchigami | A61B 6/487 | |
| 10,517,548 B2* | 12/2019 | Kojima | A61B 6/102 | |
| 10,568,597 B2* | 2/2020 | Limmer | A61B 6/467 | |
| 10,588,584 B2* | 3/2020 | Fehre | A61B 6/4405 | |

FOREIGN PATENT DOCUMENTS

| | | |
|---|---|---|
| CN | 105188538 A | 12/2015 |
| JP | H10328173 A | 12/1998 |

* cited by examiner

MEDICAL IMAGING DEVICE AND SUSPENSION GANTRY INCLUDING MULTIPLE SUPPORTING ARMS ROTATABLE RELATIVE TO EACH OTHER

CROSS REFERENCE TO RELATED APPLICATIONS

This application claims priority under 35 U.S.C. § 119 to Chinese Patent Application No. 201610458104.6 filed on Jun. 22, 2016, the entire content of which is incorporated herein by reference.

TECHNICAL FIELD

The present disclosure relates to medical imaging devices and gantries thereof in the medical field.

BACKGROUND

At present, a common medical imaging device may be an X-ray medical imaging device. A large-scale real-time X-ray medical imaging device, such as an angiographic machine, may complete the imaging of blood vessels in various parts of a body such as cardiovascular, cerebrovascular, aorta, blood vessels of abdominal organs, pelvic blood vessels, blood vessels of limbs, etc. Imaging results may have a diagnostic value to vascular lesions, tumor lesions and the like of various parts of the body. The angiographic machine may also assist in the interventional treatment of lesions in various parts of the body, such as vascular embolization of liver cancer, perfusion chemotherapy of lung cancer, embolization of cerebral aneurysm, embolization of cerebral arteriovenous malformations, balloon dilatation and stent implantation of coronary artery stenosis, occlusion of atrial septal defect and patent ductus arteriosus of congenital heart disease, balloon dilatation of mitral valve and pulmonary stenosis, dilatation and stent implantation of biliary tract and oesophagus, a variety of percutaneous biopsy and drainage, and other advanced interventional surgeries.

SUMMARY

The present disclosure provides medical imaging devices and corresponding gantries, which can satisfy more clinical application requirements.

One aspect of the present disclosure features a gantry that can be connected with a first C-arm having an imaging chain is provided. The gantry includes: a base, a second C-arm connecting the base, a second supporting arm connecting the second C-arm and being movable along the second C-arm, and a first supporting arm connecting the first C-arm, wherein, the first C-arm may be movable along the first supporting arm.

In some examples, the first supporting arm may be configured to rotate relative to the second supporting arm around an axis perpendicular to an interface connecting the first supporting arm and the second supporting arm. The first supporting arm may be an arc structure and the first C-arm may be movable along the first supporting arm. A curvature of the arc structure of the first supporting arm may be consistent with a curvature of the first C-arm, and an arc length of the arc structure of the first supporting arm may be shorter than an arc length of the first C-arm. The arc length of the arc structure of the first supporting arm may be one-sixth to two-thirds of the arc length of the first C-arm.

In some examples, the second supporting arm may be an arc structure and the second supporting arm may be movable along the second C-arm. A curvature of the arc structure of the second supporting arm may be consistent with a curvature of the second C-arm. An arc length of the arc structure of the first supporting arm may be shorter than an arc length of the second C-arm. The arc length of the arc structure of the second supporting arm may be one-sixth to two-thirds of the arc length of the second C-arm.

In an example, a curvature of the second C-arm may be smaller than a curvature of the first C-arm.

In an example, the second C-arm may be configured to rotate relative to the base around an axis perpendicular to an interface connecting the second C-arm and the base.

In an example, the gantry may be a suspension gantry and the base may be a suspension base. The gantry may further comprise a guide rail mounted on a top of an operating room, and a crane mounted on the guide rail and movable along the guide rail, wherein, the suspension base may be mounted on the crane.

In an example, the gantry is a floor gantry and the base is a floor base.

In an example, at least one third C-arm between the second C-arm and the first C-arm. The gantry may further include: a third supporting arm connecting the third C-arm, wherein, the third C-arm is movable along the third supporting arm, the third supporting arm is configured to rotate relative to the second supporting arm around a first axis perpendicular to a first interface connecting the second supporting arm and the third supporting arm, and the first supporting arm is configured to rotate relative to the third supporting arm around a second axis perpendicular to a second interface connecting the first supporting arm and the third supporting arm.

Another aspect of the present disclosure features a medical imaging device including a first C-arm having an imaging chain and a gantry connected with the first C-arm. The gantry includes a base, a second C-arm connecting the base, a second supporting arm connecting the second C-arm and being movable along the second C-arm, and a first supporting arm connecting the first C-arm, wherein, the first C-arm is movable along the first supporting arm.

In some examples, the first supporting arm may be configured to rotate relative to the second supporting arm around a first axis perpendicular to a first interface connecting the first supporting arm and the second supporting arm. The second C-arm may be configured to rotate relative to the base around a second axis perpendicular to a second interface connecting the second C-arm and the base.

In some examples, the first supporting arm is an arc structure, and the first C-arm is movable along the first supporting arm, a curvature of the arc structure of the first supporting arm is consistent with a curvature of the first C-arm, and an arc length of the arc structure of the first supporting arm is shorter than an arc length of the first C-arm.

In some examples, the second supporting arm is an arc structure, and the second supporting arm is movable along the second C-arm, a curvature of the arc structure of the second supporting arm is consistent with a curvature of the second C-arm, and an arc length of the arc structure of the first supporting arm is shorter than an arc length of the second C-arm.

In an example, the gantry is a suspension gantry and the base is a suspension base. The gantry may further comprise a guide rail mounted on a top of an operating room, and a crane mounted on the guide rail and movable along the guide rail, wherein, the suspension base is mounted on the crane.

In an example, the gantry is a floor gantry and the base is a floor base.

In an example, at least one third C-arm between the second C-arm and the first C-arm. The gantry may further include: a third supporting arm connecting the third C-arm, wherein, the third C-arm is movable along the third supporting arm, the third supporting arm is configured to rotate relative to the second supporting arm around a first axis perpendicular to a first interface connecting the second supporting arm and the third supporting arm, and the first supporting arm is configured to rotate relative to the third supporting arm around a second axis perpendicular to a second interface connecting the first supporting arm and the third supporting arm.

In the present disclosure, the first supporting arm may provide a good supporting for the first C-arm. According to the medical imaging devices provided by the present disclosure, the rotation of a large angle and a high speed for the imaging chain may be achieved, thereby satisfying more clinical application requirements.

The details of one or more embodiments of the subject matter described in the present disclosure are set forth in the accompanying drawings and description below. Other features, aspects, and advantages of the subject matter will become apparent from the description, the drawings, and the claims.

BRIEF DESCRIPTION OF DRAWINGS

FIG. 1b is a schematic diagram of a part of operating state of the medical imaging device in FIG. 1a.

FIG. 2b is a schematic diagram of a part of operating state of the medical imaging device shown in FIG. 2a.

FIG. 3b is a schematic diagram of a part of operating state of the medical imaging device shown in FIG. 3a.

FIG. 5a is a schematic diagram of a part of operating state of the medical imaging device shown in FIG. 4a.

FIG. 5b is a schematic diagram of a part of another operating state of the medical imaging device shown in FIG. 4a.

DETAILED DESCRIPTION

Combining with a scanning bed system, an X-ray medical imaging device, such as an angiographic machine, may satisfy imaging requirements of various parts of a human body from different angles by being configured with a rotatable C-arm having an imaging system (hereinafter referred to as "an imaging chain") and a gantry capable of providing rotational or translational motion. According to mounting forms, the X-ray medical imaging device may be divided into two major forms: floor and suspension.

Figure 1A:
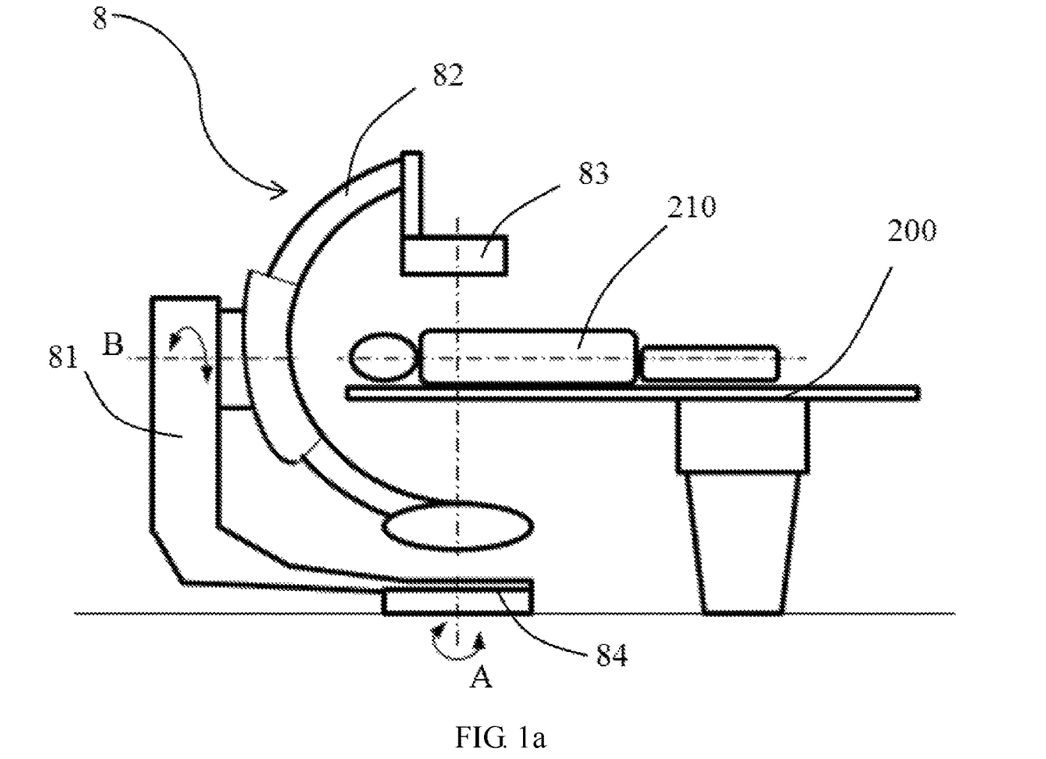
FIG. 1a is a structural schematic diagram of a medical imaging device.
Figure 1B:
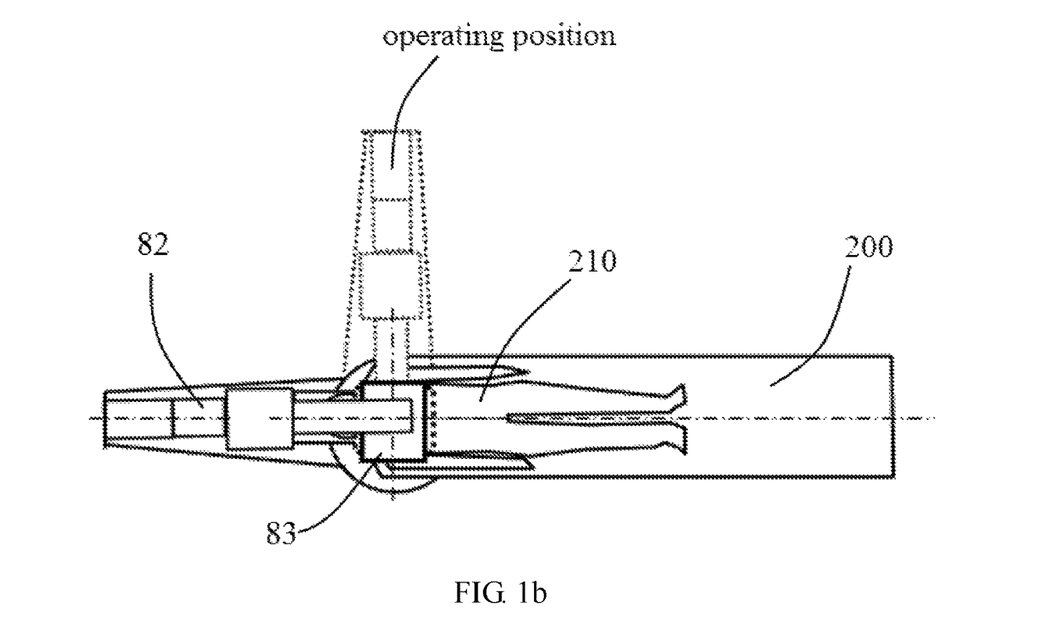

FIG. 1a is a structural schematic diagram of a medical imaging device. The following is described with an example of a floor angiographic machine 8. As shown in FIG. 1a, the floor angiographic machine 8 may include a floor gantry 81 and a rotatable C-arm 82 having an imaging chain 83. The rotatable C-arm 82 may be connected with the floor gantry 81. The floor gantry 81 may include a gantry base 84, which may be rotatable around an axis A. The rotatable C-arm 82 may be rotatable around an axis B. FIG. 1b shows a top view and a state diagram in an operating position of the floor angiographic machine 8 in FIG. 1a. The imaging chain 83 may check different positions of a subject 210 on a scanning bed 200 with the rotation of the axis A and the axis B.

Figure 2A:
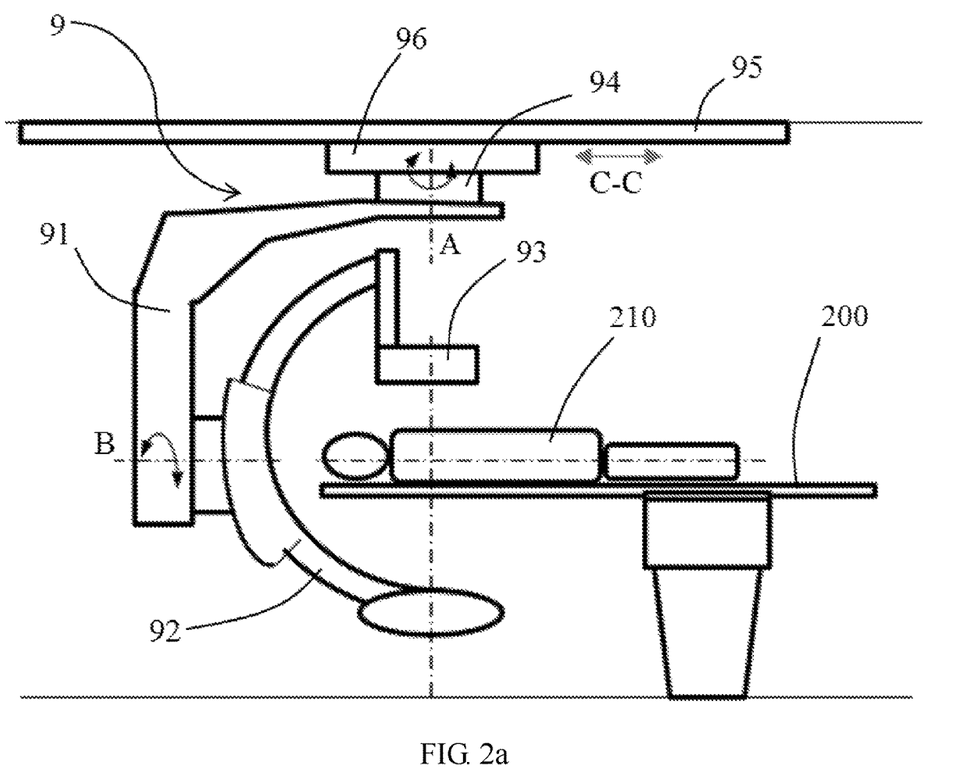
FIG. 2a is a structural schematic diagram of another medical imaging device.

FIG. 2a is a structural schematic diagram of another medical imaging device. The following is described with an example of a suspension angiographic machine 9. As shown in FIG. 2a, the suspension angiographic machine 9 may include a suspension gantry 91 and a rotatable C-arm 92 having an imaging chain 93. The rotatable C-arm 92 may be connected with the suspension gantry 91. The suspension gantry 91 may include a suspension base 94. The suspension base 94 may be provided at an upper space where the suspension angiographic machine 9 is mounted, such as a roof or an upper steel beam of an operating room. The suspension base 94 may be rotatable around the axis A. The rotatable C-arm 92 may be rotatable around an axis B. In this way, the imaging chain 93 may check different positions of the subject 210 on the scanning bed 200 with the rotation of the axis A and the axis B. Further, as shown in FIG. 2a, the suspension angiographic machine 9 may further include a guide rail 95 and a crane 96 to be mounted on the guide rail 95. The suspension base 94 may be mounted on the crane 96 by suspension.

Figure 2B:
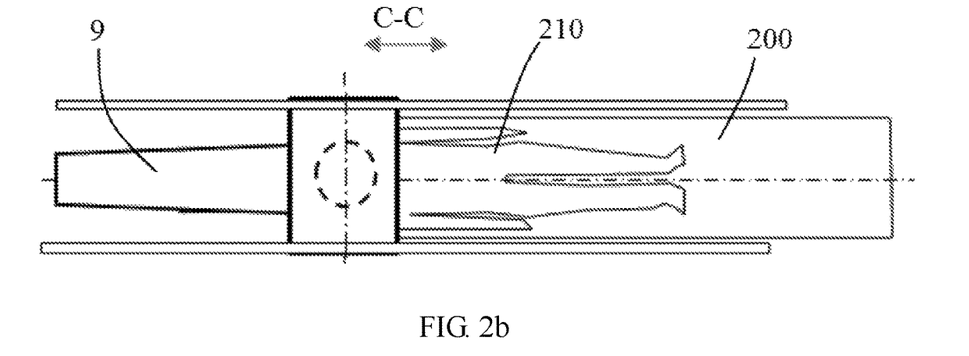

FIG. 2b shows a schematic diagram of a part of operating state of the suspension angiographic machine 9 shown in FIG. 2a. As shown in FIG. 2b, the imaging chain 93 may be moved in a direction C-C, and the movement space of the imaging chain 93 may be increased as compared to that shown in FIGS. 1a and 1b. Therefore, the suspension angiographic machine 9 may have a greater degree of freedom than the floor angiographic machine 8 in FIGS. 1a and 1b.

Figure 3A:
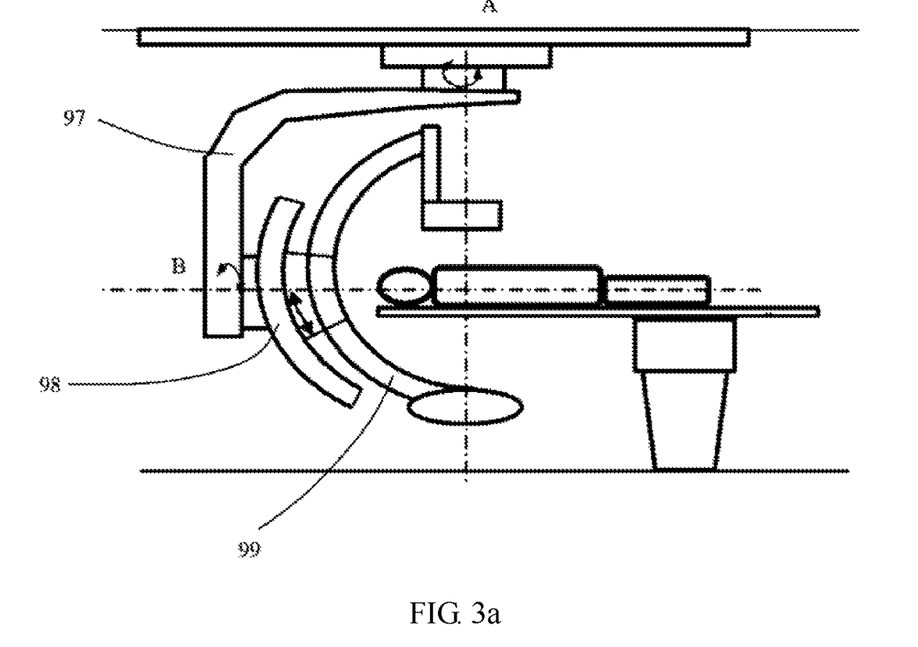
FIG. 3a is a structural schematic diagram of still another medical imaging device.
Figure 3B:
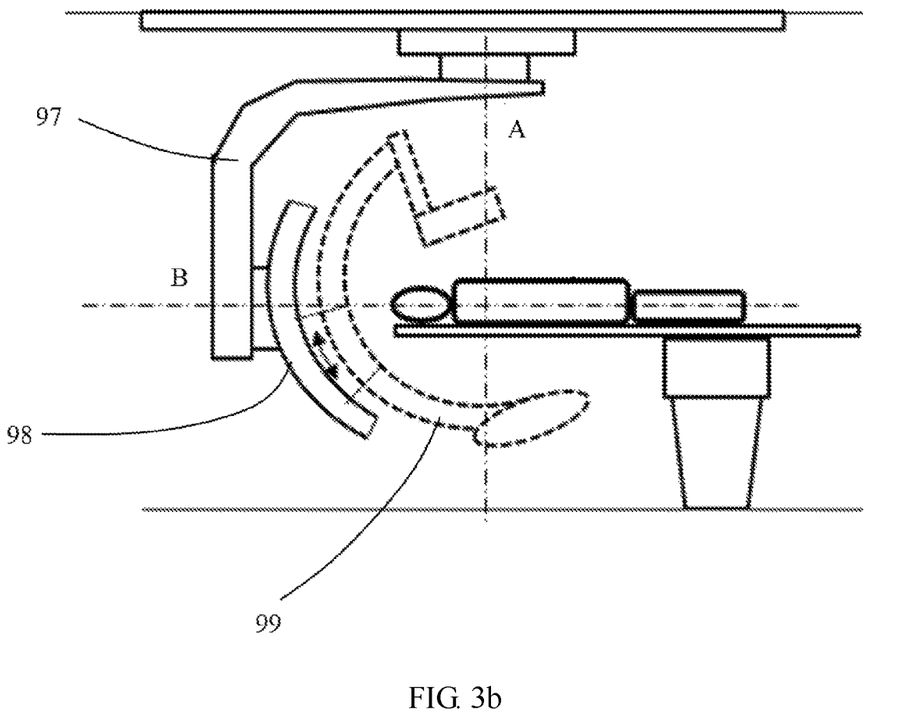

As in the examples described above, the rotation angle and speed of a single C-arm may be limited if the imaging chain position is adjusted by rotating the single C-arm. In order to realize a complicated imaging chain position, FIG. 3a shows a structural schematic diagram of still another suspension angiographic machine 9. FIG. 3b is a schematic diagram of a part of operating state of the suspension angiographic machine 9 shown in FIG. 3a. As shown in FIGS. 3a and 3b, the suspension angiographic machine 9 may have a first C-arm 99 and a second C-arm 98. The second C-arm 98 may be mounted on a gantry 97. The first C-arm 99 having an imaging chain may be mounted on the second C-arm 98 and moved relative to the second C-arm 98.

Figure 4A:
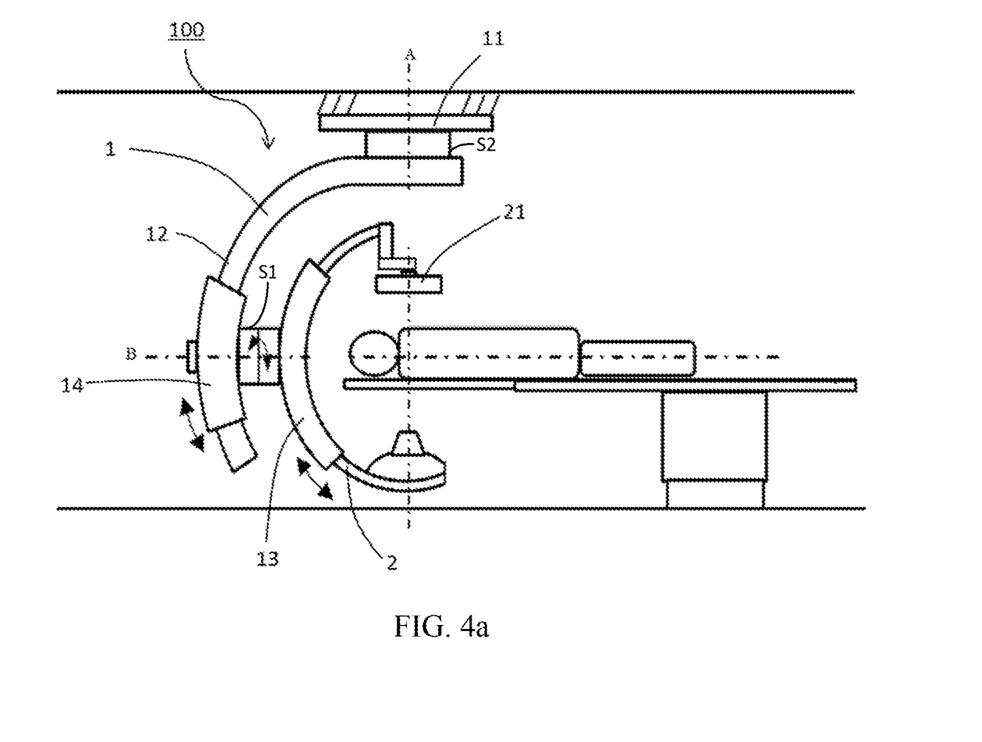
FIG. 4a is a structural schematic diagram of a medical imaging device according to an example of the present disclosure.

FIG. 4a is a structural schematic diagram of a medical imaging device 100 according to an example of the present disclosure. As shown in FIG. 4a, the medical imaging device 100 may include a gantry 1 and a first C-arm 2 having an imaging chain 21. The gantry 1 may include a base 11 and a second C-arm 12 connecting to the base 11. The second C-arm 12 may be rotatable around a first axis A. The first axis A may be perpendicular to an interface connecting the base 11 and the second C-arm 12.

The gantry 1 may also include a first supporting arm 13 connecting the first C-arm 2 and a second supporting arm 14 connecting the second C-arm 12. The first C-arm 2 may be moveable along the first supporting arm 13, and the second supporting arm 14 may be movable along the second C-arm 12.

According to an example, the first supporting arm 13 may be rotatable relative to the second supporting arm 14 around the second axis B, where the second axis B may be in a horizontal direction and perpendicular to an interface S1 connecting the first supporting arm 13 and the second supporting arm 14.

According to another example, the first supporting arm 13 may be in a shape of arc, and the first C-arm 2 may move along the first supporting arm 13. The curvature of the arc structure of the first supporting arm 13 may be consistent with the curvature of the first C-arm 2. The length of the arc structure of the first supporting arm 13 may be shorter than the arc length of the first C-arm 2. For example, the length of the arc structure of the first supporting arm 13 may be one-sixth to two-thirds of the arc length of the first C-arm 2, so that the first supporting arm 13 may provide a better supporting for the first C-arm 2 and the movement of the first C-arm 2 along the first supporting arm 13 may be smoother.

The second supporting arm 14 may be in a shape of arc, and the second supporting arm 14 may move along the second C-arm 12. The curvature of the arc structure of the second supporting arm 14 may be consistent with the curvature of the second C-arm 12. The length of the arc structure of the second supporting arm 14 may be shorter than the arc length of the second C-arm 12. For example, the length of the arc structure of the second supporting arm 14 may be one-sixth to two-thirds of the arc length of the second C-arm 12, such that the movement of the second supporting arm 14 along the second C-arm 12 may be smoother.

According to an example, a diameter of a circle in which the second C-arm 12 is located may be greater than a diameter of a circle in which the first C-arm 2 is located, i.e., the curvature of the second C-arm 12 is smaller than the curvature of the first C-arm 2.

In an example shown in FIG. 4a, the base 11 may be a suspension base 11 mounted on the top of an operating room (e.g., a roof or upper steel beam, etc.). In an example, the first axis A may be located on a centreline of the suspension base 11. A shape of the suspension base 11 may be cylindrical. The shape of the suspension base 11 may also be other shapes designed as desired, and the disclosure is not intended to be limiting to the same.

Figure 5A:
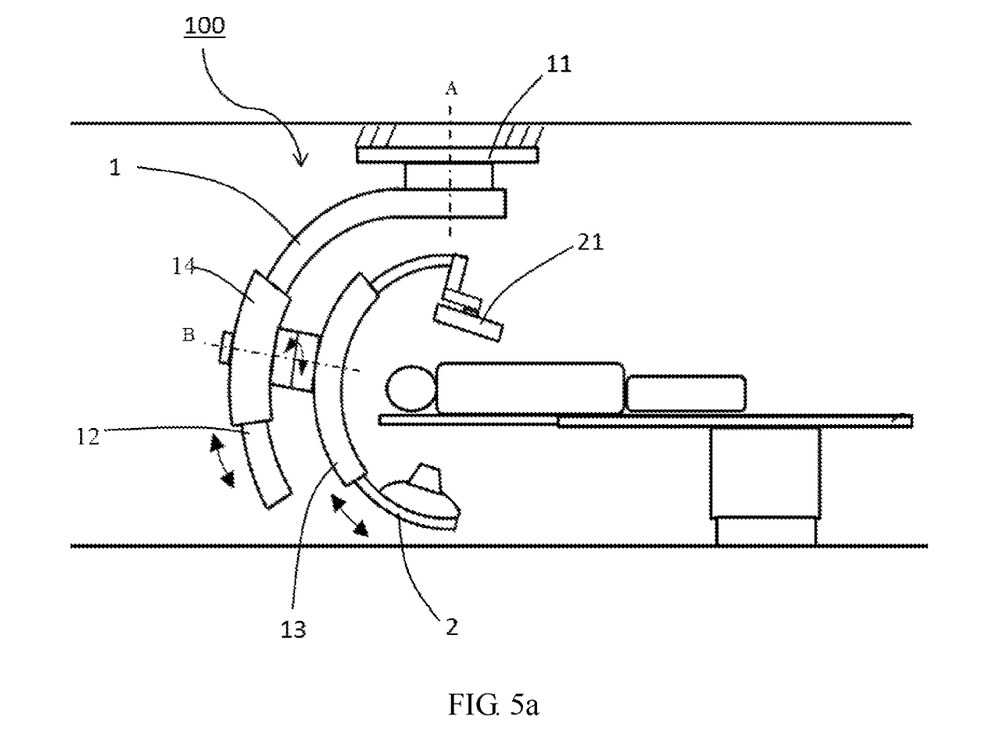
Figure 5B:
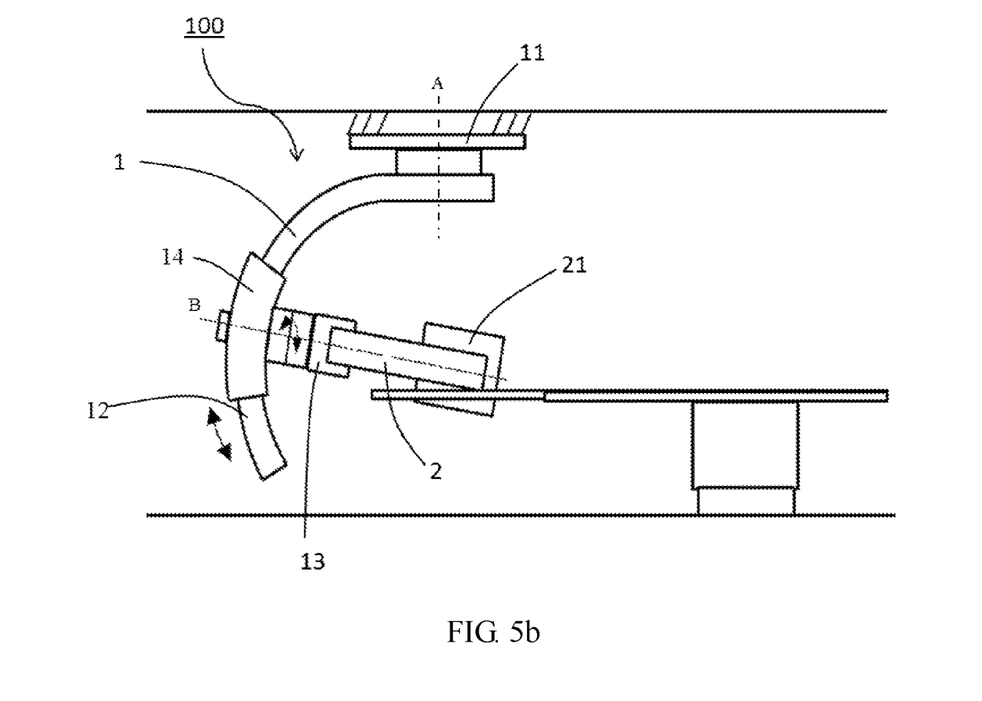

FIG. 5a is a schematic diagram of a part of operating state of the medical imaging device shown in FIG. 4a. FIG. 5b is a schematic diagram of a part of another operating state of the medical imaging device shown in FIG. 4a. In the schematic diagrams of the operating states shown in FIGS. 5a and 5b, the second supporting arm 14 may be movable along the second C-arm 12 and the first C-arm 2 may be movable along the first supporting arm 13. As shown in FIGS. 5a and 5b, the first supporting arm 13 and the first C-arm 2 may be rotatable around the second axis B relative to the second supporting arm 14. In such a way, the first C-arm 2 and the second C-arm 12 of the present disclosure may rotate relative to each other. When meeting clinical requirements, the medical imaging device 100 and the gantry 1 of the present disclosure may provide a greater rotational angle and range for the first C-arm 2 to realize a more complex imaging chain position than the suspension angiographic machine 9 of FIGS. 2a and 2b.

The relative movement between the first C-arm 2 and the first supporting arm 13, and the relative movement between the second supporting arm 14 and the second C-arm 12 may be realized by any one of a plurality of transmission methods such as a rack-and-pinion transmission, a belt transmission, a synchronous belt transmission, or an electromagnetic action.

Figure 4B:
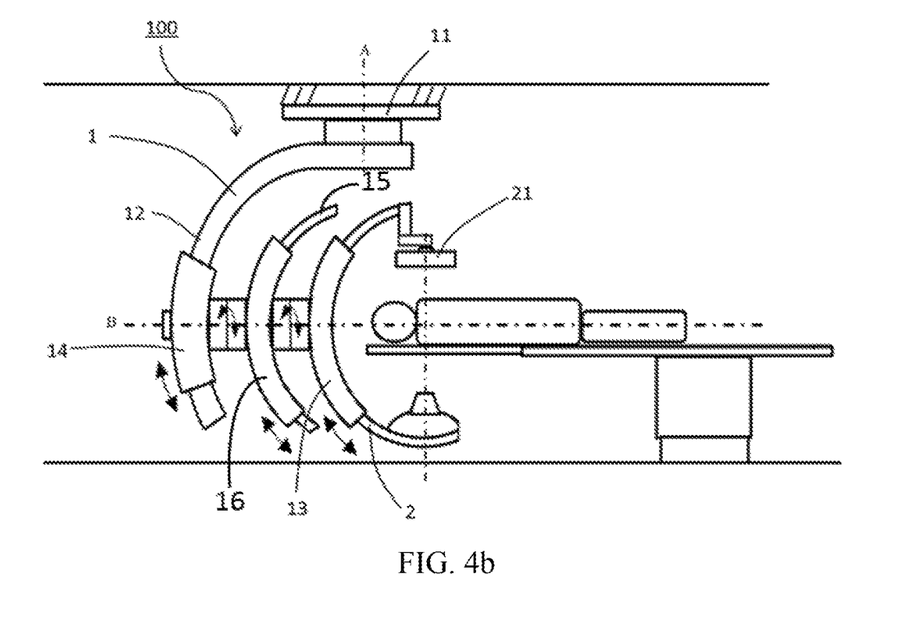
FIG. 4b is a structural schematic diagram of another medical imaging device including three C-arms according to an example of the present disclosure.

In other examples, as illustrated in FIG. 4b, there may also be at least one third C-arm 15 between the second C-arm 12 and the first C-arm 2, and there may also be a third supporting arm 16 matched with the third C-arm 15 at the same time. In some cases, the third C-arm 15 may be movable along the third supporting arm 16. The third supporting arm 16 can be configured to rotate relative to the second supporting arm 14 around an axis perpendicular to an interface connecting the second supporting arm 14 and the third supporting arm 16. The first supporting arm 13 can be configured to rotate relative to the third supporting arm 16 around an axis perpendicular to an interface connecting the first supporting arm 13 and the third supporting arm 16.

Figure 6:
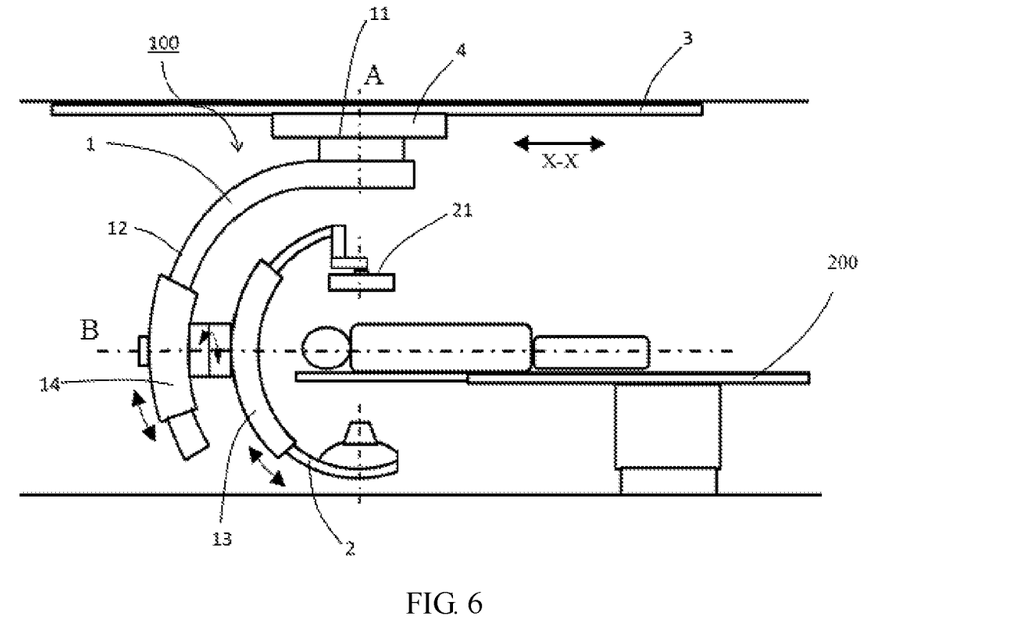
FIG. 6 is a structural schematic diagram of a medical imaging device according to another example of the present disclosure.

FIG. 6 is a structural schematic diagram of a medical imaging device according to another example of the present disclosure. As shown in FIG. 6, the gantry 1 may further include a guide rail 3 and a crane 4. The guide rail 3 may be mounted on the top of the operating room and the crane 4 may be mounted on the guide rail 3 and movable in the X-X direction. The suspension base 11 may be mounted on the crane 4. With the movement of the crane 4 on the guide rail 3, the translational movement of the imaging chain 21 in the direction X-X along the scanning bed 200 may be achieved. As a result, compared to the imaging chain 93 in the suspension angiographic machine 9 of FIGS. 2a and 2b, the imaging chain 21 may achieve a greater range of movement around the scanning bed 200, and more advanced clinical application requirements may be met.

Figure 7:
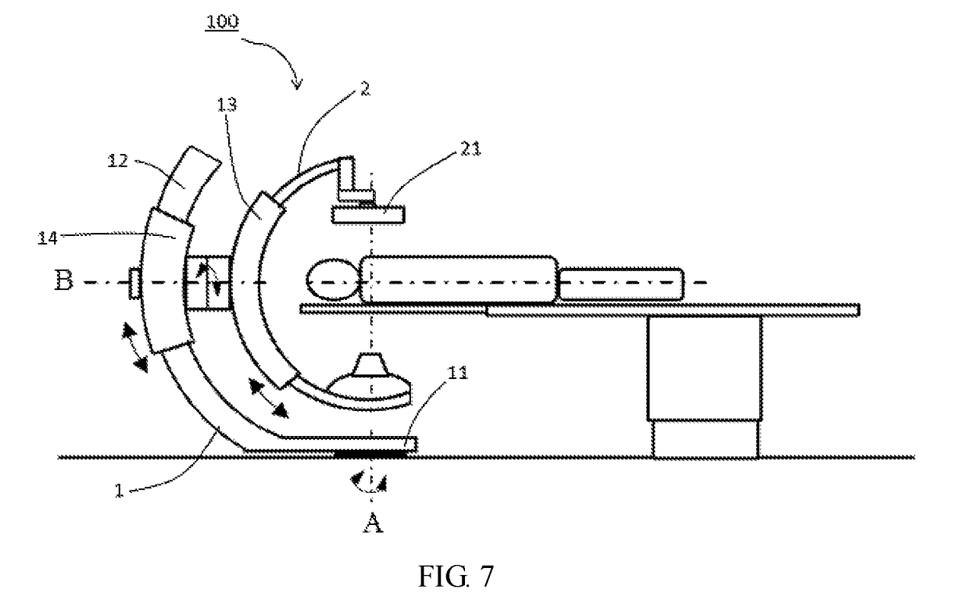
FIG. 7 is a structural schematic diagram of a medical imaging device according to still another example of the present disclosure.

FIG. 7 is a structural schematic diagram of a medical imaging device according to still another example of the present disclosure. As shown in FIG. 7, the base 11 of the gantry 1 may include a floor base mounted on the floor for replacing the suspension base as in the above examples. The remaining structure may be unchanged. In this way, in addition to enabling the medical imaging device 100 to obtain the rotation of a large angle and a high speed for the imaging chain in the above-described examples, the structural stability may be improved, and the cost and mounting difficulty may be reduced.

In examples of the present disclosure as described above, a control on the rotation of the first axis A and the second axis B may be either electrical or partially or entirely manual. To hold an image in a normal position, the imaging chain 21 may also rotate with the rotation of the first axis A and/or the second axis B.

In the foregoing description, details of technical solutions of the present disclosure have been set forth. However, those skilled in the art will recognize that the present disclosure is not limited to specific details set forth in above examples, but may change within a scope defined by the claims.

The foregoing is intended only as preferred examples of the present disclosure and is not intended to be limiting of the present disclosure, and any modifications, equivalent substitutions, improvements and the like within the spirit and principle of the present disclosure are intended to be comprised within a scope of protection of the present disclosure.

The invention claimed is:

1. A gantry of a medical imaging device comprising:
a base,
a first supporting arm configured to connect a first C-arm of the medical imaging device, the first C-arm being movable along the first supporting arm and having an imaging system,
a second C-arm connecting the base,
a second supporting arm configured to connect the second C-arm and to be movable along the second C-arm; and
a first interface connecting the first supporting arm and the second supporting arm,
wherein the first supporting arm is configured to rotate relative to the second supporting arm around a first axis perpendicular to the first interface.

2. The gantry according to claim 1, wherein,
the first supporting arm comprises an arc structure, and
the first C-arm is movable along the first supporting arm.

3. The gantry according to claim 2, wherein,
a curvature of the arc structure of the first supporting arm is consistent with a curvature of the first C-arm, and
an arc length of the arc structure of the first supporting arm is shorter than an arc length of the first C-arm.

4. The gantry according to claim 3, wherein the arc length of the arc structure of the first supporting arm is one-sixth to two-thirds of the arc length of the first C-arm.

5. The gantry according to claim 1, wherein,
the second supporting arm comprises an arc structure, and
the second supporting arm is movable along the second C-arm.

6. The gantry according to claim 5, wherein,
a curvature of the arc structure of the second supporting arm is consistent with a curvature of the second C-arm, and
an arc length of the arc structure of the second supporting arm is shorter than an arc length of the second C-arm.

7. The gantry according to claim 6, wherein the arc length of the arc structure of the second supporting arm is one-sixth to two-thirds of the arc length of the second C-arm.

8. The gantry according to claim 1, wherein a curvature of the second C-arm is smaller than a curvature of the first C-arm.

9. The gantry according to claim 1, further comprising:
a second interface connecting the second C-arm and the base,
wherein the second C-arm is configured to rotate relative to the base around a second axis perpendicular to the second interface.

10. The gantry according to claim 1, wherein the base comprises a suspension base mounted on a top of an operating room.

11. The gantry according to claim 10, further comprising:
a guide rail mounted on the top of the operating room; and
a crane mounted on the guide rail and movable along the guide rail, wherein the suspension base is mounted on the crane.

12. The gantry according to claim 1, wherein the base comprises a floor base mounted on a floor of an operating room.

13. The gantry according to claim 1, further comprising:
a third C-arm between the second C-arm and the first C-arm.

14. The gantry according to claim 13, further comprising:
a third supporting arm connecting the third C-arm,
a second interface connecting the second supporting arm and the third supporting arm, and
a third interface connecting the first supporting arm and the third supporting arm,
wherein,
the third C-arm is movable along the third supporting arm,
the third supporting arm is configured to rotate relative to the second supporting arm around a second axis perpendicular to the second interface, and
the first supporting arm is configured to rotate relative to the third supporting arm around a third axis perpendicular to the third interface.

15. A medical imaging device, comprising:
a first C-arm having an imaging chain; and
a gantry connected with the first C-arm, comprising:
a base,
a second C-arm connecting the base,
a first supporting arm connecting the first C-arm, wherein the first C-arm is movable along the first supporting arm,
a second supporting arm connecting the second C-arm and being movable along the second C-arm, and
a first interface connecting the first supporting arm and the second supporting arm,
wherein the first supporting arm is configured to rotate relative to the second supporting arm around a first axis perpendicular to the first interface.

16. The medical imaging device according to claim 15, further comprising:
a second interface connecting the second C-arm and the base,
wherein the second C-arm is configured to rotate relative to the base around a second axis perpendicular to the second interface.

17. The medical imaging device according to claim 15, wherein,
the first supporting arm comprises an arc structure, and
the first C-arm is movable along the first supporting arm,
a curvature of the arc structure of the first supporting arm is consistent with a curvature of the first C-arm, and
an arc length of the arc structure of the first supporting arm is shorter than an arc length of the first C-arm.

18. The medical imaging device according to claim 15, wherein,
the second supporting arm comprises an arc structure, and the second supporting arm is movable along the second C-arm,
a curvature of the arc structure of the second supporting arm is consistent with a curvature of the second C-arm, and
an arc length of the arc structure of the second supporting arm is shorter than an arc length of the second C-arm.

19. The medical imaging device according to claim 15, wherein the base comprises a suspension base mounted on a top of an operating room, and
the gantry further comprises:
a guide rail mounted on the top of the operating room; and
a crane mounted on the guide rail and movable along the guide rail, wherein the suspension base is mounted on the crane.

20. The medical imaging device according to claim 15, wherein a curvature of the second C-arm is smaller than a curvature of the first C-arm.

* * * * *